United States Patent [19]
Casten et al.

[11] 4,182,763
[45] Jan. 8, 1980

[54] BUSPIRONE ANTI-ANXIETY METHOD

[75] Inventors: George P. Casten; Gordon R. McKinney; Roger E. Newton; E. Crosby Tompkins, all of Evansville; John H. Weikel, Jr., Mt. Vernon, all of Ind.

[73] Assignee: Mead Johnson & Company, Evansville, Ind.

[21] Appl. No.: 908,597

[22] Filed: May 22, 1978

[51] Int. Cl.² ............................................. A61K 31/505
[52] U.S. Cl. ..................................................... 424/251
[58] Field of Search ......................................... 424/251

[56] References Cited
U.S. PATENT DOCUMENTS 3,717,634  2/1973  Wu et al. ...................... 260/256.4 N
3,976,776  8/1976  Wu et al. .............................. 424/251

OTHER PUBLICATIONS

Wu et al., J. Med. Chem. 15, (1972), pp. 477–479.
Allen et al., Arzneim-Forsch, 24, No. 6, 917–992 (1974).
Sathancenthan et al., Current Therapeutic Research, 18, (5), 701–705 (1975).

Primary Examiner—Stanley J. Friedman
Attorney, Agent, or Firm—R. E. Carnahan; R. H. Uloth

[57] ABSTRACT

Buspirone hydrochloride is an effective anti-anxiety agent for the palliative treatment of neurotic patients in which symptoms of anxiety are predominant at doses which are without observable effect in either normal individuals or psychotic patients.

9 Claims, No Drawings

BUSPIRONE ANTI-ANXIETY METHOD

FIELD OF THE INVENTION

This invention is concerned with a drug bio-affecting and body-treating process which employs the pyrimidine compound 8-[4-[4-(2-pyrimidinyl)-1-piperazinyl]-butyl]-8-azaspiro[4.5]decane-7,9-dione or a pharmaceutically acceptable acid addition salt thereof (Class 424, Subclass 251).

DESCRIPTION OF THE PRIOR ART

The pyrimidine compound with which the present invention is concerned has the following structural formula

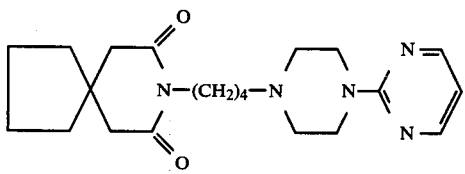

The hydrochloride salt has been referred to in the prior art as MJ 9022-1 and as buspirone hydrochloride. Other acid addition salts thereof are named by combining "buspirone" with the appropriate word to define the acid from which it is prepared as in "buspirone hydrochloride." The latter is the United States Adopted Name (USAN). Refer to J. Amer. Med. Assoc. 225, 520 (1973).

The synthesis of the compound and the identification of its psychotropic properties typical of the major tranzuilizers such as chlorpramazine are described in the following patents and publications.

1. Y. H. Wu, et al., J. Med. Chem. 15, 477 (1972) "Psychosedative Agents. 2. 8-(4-Substituted 1-Piperazinylalkyl)-8-azaspiro[4.5]decane-7,9-diones".

2. Y. H. Wu, et al., U.S. Pat. No. 3,717,634 patented Feb. 20, 1973. "N-(Heteroarcyclic)piperazinylalkyl-azaspiroalkanediones".

3. L. E. Allen, et al., Arzneim.-Forsch. 24, Nr. 6, 917–922 (1974). "Pharmacologic Effects of MJ 9022-1, a Potential Tranquilizing Agent."

4. G. L. Sathananthan, et al., Current Therapeutic Research, 18, (5), 701-705 (1975). "MJ 9022: Correlation Between Neuroleptic Potential and Stereotypy."

5. Y. H. Wu, et al., U.S. Pat. No. 3,976,776 patented Aug. 24, 1976. "Tranquilizer Process Employing N-(Heteroarcyclic)piperazinylalkylazaspiroalkanediones."

SUMMARY OF THE INVENTION

The process of the present invention is intended for the palliative treatment of neurosis with buspirone or a pharmaceutically acceptable acid addition salt thereof where anxiety symptoms are prominent. Pharmaceutically acceptable acid addition salts of buspirone and methods of pharmaceutical formulation are described in the above patent (2) of Y. H. Wu, et al., U.S. Pat. No. 3,717,634 which is incorporated herein in its entirety by reference. The process is specifically intended for adult patients who present with manifest anxiety characterized by an affective state which may occur under many clinical circumstances and in diverse pathologic contexts. It is also applicable to children in similar circumstances.

Neurosis is a functional nervous disorder without demonstrable physical lesion. Neuroses are defined in "Diagnostic and Statistical Manual of Mental Disorders" 2nd Edition, published by American Psychiatric Association, 1968 (Library of Congress Catalog No. 6826515) as follows (page 39).

"Anxiety is the chief characteristic of the neuroses. It may be felt and expressed directly, or it may be controlled unconsciously and automatically by conversion, displacement and various other psychological mechanisms. Generally, these mechanisms produce symptoms experienced as subjective distress from which the patient desires relief.

"The neuroses, as contrasted to the psychoses, manifest neither gross distortion or misinterpretation of external reality, nor gross personality disorganization. A possible exception to this is hysterical neurosis, which some believe may occasionally be accompanied by hallucinations and other symptoms encountered in psychoses.

"Traditionally, neurotic patients, however severely handicapped by their symptoms, are not classified as psychotic because they are aware that their mental functioning is disturbed."

Anxiety neurosis is defined in the same reference as follows (page 39).

"This neurosis is characterized by anxious over-concern extending to panic and frequently associated with somatic symptoms. Unlike Phobic neurosis (q.v.), anxiety may occur under any circumstances and is not restricted to specific situations or objects. This disorder must be distinguished from normal apprehension or fear, which occurs in realistically dangerous situations."

The present process is concerned with the treatment of anxiety neuroses, and is to be distinguished from prior psychotherapeutic processes employing buspirone which dealt with psychoses. The following definition of psychoses is quoted from the above cited "Diagnostic and Statistical Manual of Mental Disorders" for the purpose of differentiating "psychoses" from "neuroses."

"Patients are described as psychotic when their mental functioning is sufficiently impaired to interfere grossly with their capacity to meet the ordinary demands of life. The impairment may result from a serious distortion in their capacity to recognize reality. Hallucinations and delusions, for example, may distort their perceptions. Alterations of mood may be so profound that the patient's capacity to respond appropriately is grossly impaired. Deficits in perception, language and memory may be so severe that the patient's capacity for mental grasp of his situation is effectively lost."

Different classes of drugs have been used in the past for the treatment of neuroses and psychoses and no relationship has developed among the drugs which are applicable to the treatment of these two distinct conditions. The psychoses are mainly treated with the phenothiazines with chloropromazine being representative of this class. The anti-anxiety agents or anxiolytics are drawn from a number of structural classes but the benzodiazepines, with diazepam as a specific example, include the majority of drugs used for this purpose. Buspirone is structurally unrelated to any other drug used in the treatment of neuroses.

Administration of buspirone according to the present invention may be by the parenteral, oral, or rectal routes. The oral route is, however, preferred and there is, in fact, little need to employ other means of administration such as subcutaneous, intramuscular, or intravenous injection. The reason for this is that neurotic patients for whom the process is applicable are rational individuals, are generally treated on an out-patient basis, and are able to cooperate with the physician or psychiatrist. Generally speaking, the effectiveness of the method soon becomes evident to the patient and ensures his cooperation.

Dosage amounts are less than about 100 mg. per day and preferably in the range of 20-30 mg. per day. In exceptional cases, it may be necessary to increase the dose to about 60 mg. per day. Since the dosage must be tailored to the individual patient, the usual practice is to commence with a dose of 5 mg. administered two or three times per day and to then increase the dose every two or three days by 5 mg. at each dosage time until the desired response is observed or until the patient complains of side effects. Single daily dosage is applicable in some instances. The duration of treatment is extended until the patient's symptoms have substantially disappeared and a symptom-free period has elapsed. Usual periods of treatment are from one to three months. Treatment may be re-instituted at any time that symptoms reappear.

The dosage range referred to above serves to emphasize the distinction between the present process and the treatment of psychotic patients with buspirone as has been described in the prior art (G. L. Sathananthan, et al. op cit.) in which doses of from 600 to 2400 mg. per day of buspirone hydrochloride were required to demonstrate neuroleptic action in psychotic patients. The dosage range of 10 to 100 mg. per day which is applicable to neurotic patients to achieve an anxiolytic effect is without adverse effect in a normal individual and without neuroleptic effect in a psychotic patient for whom treatment with an anti-psychotic agent or major tranquilizer is indicated.

DETAILED DESCRIPTION OF THE INVENTION

The patients for treatment according to the present invention are minimally characterized by the first two manifestations listed below which are exhibited to a modrate or high degree of severity and preferably at least three of the others listed as (3) through (17).

Subjective Experiences:
(1) Feeling nervous, jittery, jumpy
(2) Feeling fearful, apprehensive, anxious, panicky
(3) Fears of fainting, screaming, losing control, crowds, places, disaster, death
(4) Avoiding certian places, things, or activities because of fear
(5) Feeling tense or keyed up
Muscular or Motor Phenomena:
(6) Tense, aching muscles
(7) Trembling, shaking
(8) Restlessness, fidgeting
Autonomic Phenomena:
(9) Heart beating fast or pounding; chest pain
(10) Trouble catching breath, air hunger, smothering, lump in throat, choking
(11) Sweating, especially armpits, palms, soles of feet
(12) Cold, clammy hands
(13) Dry mouth
(14) Dizziness, faintness, lightheadedness, weakness
(15) Tingling feelings in hands or feet
(16) Stomach "gas", nausea, upset stomach
(17) Frequency or urgency of bladder or bowels The patients are preferably rated before commencing treatment according to one or more of the established psychometric rating scales for neurotic patients. The same psychometric methods may then be used to evaluate the patient periodically during the treatment period, preferably every 2 or 3 days until the appropriate dosage schedule has been determined and then at weekly intervals.

Various suitable rating scales have been described in the literature. They have been collected in a form readily adapted to clinical use by the U.S. Department of Health, Education and Welfare in a volume by William Guy entitled "ECDEU Assessment Mannual for Psychopharmacology," Revised 1976, National Institute of Mental Health, 5600 Fishers Lane, Rockville, Maryland 20852 (DHEW Publication No. (ADM)76-338). ECDEU is an acronym for Early Clinical Drug Evaluation Unit. Some of these psychometric rating scales which are suitable for this invention are listed below. The page numbers refer to the foregoing collection.

| | |
|---|---|
| Hamilton Anxiety Scale | page 193 |
| Hamilton Depression Scale | page 179 |
| Self Report Symptom Inventory | page 313 |
| Profile of Mood States | page 529 |
| Hopkins Symptom Checklist | page 575 |
| Self Rating Symptom Scale | page 579 |
| Clinical Global Impressions | page 217 |

Other Rating scales as may suit the psysician or psychiatrist may also be employed. Also, other tests as may be deemed desirable by the physician or psychiatrist in accord with good medical practice should be employed such as a complete medical history and physical examination.

Dosage is commenced at from 10 mg. to 20 mg. per day, and then increased step-wise until an anxiolytically effective dose is achieved without toxic effect. The dose may then be reduced to establish the optimal effect-minimal dose relationship. This usually occurs in the range of 20-30 mg. per day, but doses as high as 60 mg. per day may be employed. Doses as high as about 100 mg. are without substantial adverse effects in normal or neurotic individuals. Dosage on a b.i.d. or t.i.d. schedule is preferred.

DESCRIPTION OF SPECIFIC EMBODIMENTS

EXAMPLE 1

Open Study.—Thirty patients diagnosed as suffering from anxiety reaction were entered into an evaluation of buspirone hydrochloride for treatment of the condition. Seven of the thirty patients also exhibited significant symptoms of depression in addition to their predominating symptoms of anxiety reaction. The duration of the study was four weeks. Seven patients dropped out of the study and were not included in the analysis of the results. Two of these suffered side effects by the second day of treatment, one was improved by the seventh day of treatment, and the other four were lost to follow-up for unknown reasons. All patients entered into the study had a rating on the Hamilton Anxiety Scale (op. cit.) of at least 18 on entry into the study. Anxiety symptoms had been present for at least a month in all cases, and 19 had suffered the symptoms for a year or more. None of the patients exhibited evidence of schizophrenia, affective psychosis, convulsive disorders, organic brain syndrome, strong sociopathy, drug addiction, or alcoholism. The patients were rated on entry into and at the conclusion of the study and weekly according to the Hamilton Anxiety Scale (HAM-A op. cit.), the Hamilton Depression Scale (HAM-D op. cit.), and by a physician's questionaire (PQ) according to which severity of the disease was rated on the following scale: 1—not ill; 2—very mild; 3—mild; 4—moderate; 5 moderately severe; 6—severe; 7—extremely severe. Other rating methods were also used. The following table shows the average daily dose, and the rating scale results. The HAM-A and HAM-D ratings at the end of the study were within the normal range, and the PQ rating indicated only very mild remaining anxiety.

| PHYSICIAN AND PATIENT EVALUATION OF THERAPEUTIC EFFECT | | | | | | | | |
|---|---|---|---|---|---|---|---|---|
| | No. Patients | | Therapeutic Effect at Termination (No. Patients) | | | | | Average Daily Dose (mg.) |
| | | | Physician Evaluation | | | Patient Evaluation | | |
| Treatment At: | In Study | Dropout | Marked | Moderate | Minimal | Much | Moderately | A Little | |
| END OF STUDY | | | | | | | | | |
| Buspirone | 14 | 6[1] | 8 | 4 | 2 | 10 | 1 | 3 | 23.7[5] |
| Diazepam | 14 | 6[2] | 7 | 4 | 3 | 9 | 2 | 3 | 26.4[5] |
| Placebo | 10 | 10[3] | 1 | 2 | 7 | 3 | — | 7 | |
| CUMULATIVE RESULTS: | | | | | | | | | |
| Buspirone | 18 | 2[4] | 10 | 4 | 3 | 12 | 3 | 3 | 19.6 |
| Diazepam | 20 | none | 7 | 6 | 7 | 10 | 3 | 7 | 18.7 |
| Placebo | 18 | 2[4] | 1 | 2 | 15 | 3 | — | 15 | |

[1] One dropped out because of side effects; one due to unrelated illness; two because of improvement; two for unknown reasons.
[2] Three dropped out because of side effects; one due to unrelated changed life situation; two because of improvement.
[3] Two dropped out during the first week for unknown reasons; the remainder dropped out subsequently due to lack of improvement.
[4] Drop-outs where no interim evaluation was obtained.
[5] During fourth week.

| AVERAGE ANXIETY RATINGS AND DOSAGES | | | | |
|---|---|---|---|---|
| | Daily Dose (mg.) | HAM-A | HAM-D | PQ | $n^3$ |
| Outset | 0 | 21.5 | 12.1 | 4.5 | 23 |
| Week 1 | 21.3 | 11.0[1] | 8.8[2] | 3.6[2] | 23 |
| Week 2 | 25.1 | 8.3[1] | 7.4[2] | 2.9[2] | 16 |
| Week 3 | 24.1 | 5.5[1] | 4.8[1] | 2.5[2] | 13 |
| Week 4 | 19.9 | 2.8[1] | 3.7[1] | 2.3[2] | 12 |

[1] Paired t-test relative to outset values significant @ 0.01 level.
[2] Paired t-test relative to outset values significant @ 0.05 level.
[3] Number of patients included in evaluation.

EXAMPLE 2

Double Blind Study.—Sixty adult out-patients with manifest anxiety were selected for a double-blind parallel study. Twenty patients were entered into each of three groups. One group was treated with buspirone hydrochloride, 5 mg. capsule, another with diazepam, 5 mg. tablet contained within a matching capsule, and the third with placebo, inert ingredients in a matching capsule. The starting dose was one capsule b.i.d. (buspirone hydrochloride 10 mg. or diazepam 10 mg.) and the dose was increased by one or two capsules every two or three days depending upon therapeutic response and side effects. The maximum dose allowable was 60 mg. per day of buspirone hydrochloride or diazepam. Laboratory and physical examinations were conducted on admission and at termination of the study and a number of standard psychometric rating scales were administered on admission, at weekly intervals, and at termination of the study. The study duration was four weeks. The results based upon the degree of improvement in the physician's evaluation and in the patient's own evaluation are given in the following table. The status of the patients at the end of the study is given, as well as the cumulative results which include drop-outs evaluated at an interim period.

The therapeutic effect with buspirone hydrochloride was comparable to that obtained with diazepam. Buspirone had fewer side effects than either diazepam or placebo. Only three patients complained of side effects under buspirone. These occurred within the first two weeks and only one patient dropped out because of side effects (moderate dizziness, cold sweat). Ten patients complained of side effects under diazepam but only three dropped out for this reason (weakness, tiredness, nausea, vomiting, insomnia, vivid dreams, drowsiness, depression, dry mouth, dizziness, excitement, confusion, tachycardia, tremor, blurred vision, and headache). Six patients complained of side effects under placebo but none dropped out for this reason. Placebo drop-outs were due to lack of therapeutic effect. In addition, buspirone appeared to be effective in relieving depression in patients presenting with mixed anxiety and depression symptoms. Sleep information gathered during the study indicated that the patients slept more deeply under diazepam in contrast to the lighter sleep reported by the buspirone patients. A deeper sleep would accord with the sedation action of diazepam.

EXAMPLE 3

Buspirone Hydrochloride 5 mg. and 10 mg. Tablets.-The following ingredients are employed.

| | 5 mg. Tablet | 10 mg. Tablet |
|---|---|---|
| Buspirone Hydrochloride | 5.0 mg | 10.0 mg |
| Lactose, Anhydrous Direct compression | 55.7 | 111.4 |
| Starch, Sodium Carboxy-Methyl | 8.0 | 16.0 |
| Cellulose, Microcrystalline, NF | 30.0 | 60.0 |
| Colloidal Silicon Dioxide | 0.5 | 1.0 |
| Magnesium Stearate | 0.8 | 1.6 |
| TOTAL | 100.0 | 200.0 |

Processing Instructions:
1.0 Blend in a suitable mixer:
  (a) Colloidal Silicon Dioxide
  (b) Cellulose, Microcrystalline, NF
2.0 Pass the blended material from Step 1 through a screen.
3.0 Blend in a suitable mixer:
  (a) Screened powder from Step 2

(b) Buspirone Hydrochloride
(c) Lactose, Anhydrous DC
(d) Starch, Sodium Carboxy-Methyl
(e) Cellulose, Microcrystalline, NF
(f) Magnesium Stearate 4.0 Compress the granulation into tablets.

What is claimed is:

1. A method for the palliative treatment of neurosis in which anxiety symptoms are prominent which comprises administering a non-toxic anxiolytically effective dose of buspirone or a pharmaceutically acceptable acid addition salt thereof to a neurotic patient.

2. The method of claim 1 wherein buspirone hydrochloride is employed, and dosage is by the oral route.

3. The method of claim 2 wherein said patient is suffering from anxiety neurosis.

4. The method of claim 2 wherein said patient is suffering from anxiety neurosis with depressive symptoms.

5. The method of claims 2, 3, or 5 wherein said patient is an adult and a daily dose of from 10 mg. to 60 mg. is employed.

6. The method of claim 5 wherein said daily dose is divided and administered b.i.d.

7. The method of claim 5 wherein said daily dose is divided and administered t.i.d.

8. The method of claim 2 wherein the maximum total daily dose of up to about 100 mg.

9. The method of claims 2, 3, or 4 wherein said patient is an adult and a daily dose of from 20 mg. to 30 mg. is employed.

* * * * *

UNITED STATES PATENT AND TRADEMARK OFFICE
Certificate

Patent No. 4,182,763            Patented January 8, 1980

On petition requesting issuance of a certificate for correction of inventorship pursuant to 35 USC 256, it has been found that the above-identified patent, through error and without any deceptive intent, improperly sets forth the inventorship. Accordingly, it is hereby certified that the correct inventorship of this patent is George P. Casten, Gordon R. McKinney, Roger E. Newton, E. Crosby Tompkins, John H. Weikel, Jr. and John E. Gajewski.

Signed and Sealed this Eighteenth Day of March 1986.

BRADLEY R. GARRIS,
*Office of the Deputy Assistant Commissioner for Patents.*

UNITED STATES PATENT AND TRADEMARK OFFICE
CERTIFICATE OF CORRECTION

PATENT NO. : 4,182,763

DATED : January 8, 1980

INVENTOR(S) : George P. Casten et al.

It is certified that error appears in the above-identified patent and that said Letters Patent is hereby corrected as shown below:

Column 8, line 5, Claim 5, delete "2, 3 or 5" and insert -- 2, 3 or 4 --.

Signed and Sealed this

Eighth Day of July 1986

[SEAL]

Attest:

DONALD J. QUIGG

Attesting Officer

Commissioner of Patents and Trademarks

UNITED STATES PATENT AND TRADEMARK OFFICE

CERTIFICATE EXTENDING PATENT TERM
UNDER 35 U.S.C. 156

Patent No.    : 4,182,763

Dated         : January 8, 1980

Inventor(s)   : George P. Casten, et al

Patent Owner  : Mead Johnson & Company

This is to certify that there has been presented to the

COMMISSIONER OF PATENTS AND TRADEMARKS an application under 35 U.S.C. 156 for an extension of the patent term. Since it appears that the requirements of law have been met, this certificate extends the term of the patent for the period of

2 YEARS with all rights pertaining thereto as provided by 35 USC 156(b).

I have caused the seal of the Patent and Trademark Office to be affixed this First day of October 1987.

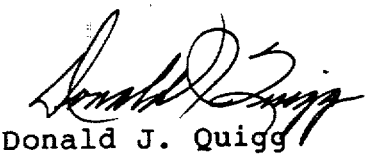

Donald J. Quigg

Assistant Secretary and Commissioner of Patents and Trademarks